United States Patent [19]

Feng

[11] Patent Number: 4,510,812
[45] Date of Patent: Apr. 16, 1985

[54] APPARATUS FOR ACOUSTIC EMISSION DETECTION INCLUDING A WAVEGUIDE MADE OF ALUMINUM OR BERYLLIUM OXIDE

[75] Inventor: Ching C. Feng, San Juan Capistrano, Calif.

[73] Assignee: Dunegan Corporation, Knoxville, Tenn.

[21] Appl. No.: 451,581

[22] Filed: Dec. 20, 1982

[51] Int. Cl.³ ............................................. G01N 29/00
[52] U.S. Cl. ............................................. 73/644; 73/587
[58] Field of Search .................. 73/644, 587; 310/336, 310/334

[56] References Cited

U.S. PATENT DOCUMENTS

| 2,494,433 | 1/1950 | Erwin | 310/336 |
| 3,177,381 | 4/1965 | Bosselaar | 310/336 |
| 3,922,622 | 11/1975 | Boyd et al. | 310/334 X |
| 3,934,460 | 1/1976 | Sherwin | 310/336 X |
| 4,208,602 | 6/1980 | Stoller | 310/336 X |
| 4,208,917 | 6/1980 | Aoyama | 73/644 |
| 4,297,607 | 10/1981 | Lynnworth | 310/336 X |
| 4,392,380 | 7/1983 | Caines | 73/644 |

Primary Examiner—Stephen A. Kreitman
Assistant Examiner—Vincent P. Kovalick
Attorney, Agent, or Firm—Knobbe, Martens, Olson & Bear

[57] ABSTRACT

A waveguide is provided, particularly for use in acoustic emission applications involving a hostile environment, comprised of a member selected from the group consisting of aluminum oxide and beryllium oxide. The waveguide is solid in form, and varies in length depending upon the specific application or use of the waveguide and the frequency of the signal. Size varies inversely to frequency levels. The cross sectional dimension will vary depending upon application, and will generally conform to the size of the crystal sensor element being utilized in a particular application.

5 Claims, 6 Drawing Figures

APPARATUS FOR ACOUSTIC EMISSION DETECTION INCLUDING A WAVEGUIDE MADE OF ALUMINUM OR BERYLLIUM OXIDE

BACKGROUND AND STATEMENT OF THE INVENTION

This invention relates generally to improvements in electromechanical acoustic emission detectors or transducers for detecting acoustic emission signals that are emitted from solid objects with those signals being caused by cracking or failure in some way in the solid object of interest. The signals obtained are converted into electrical signals having components of corresponding frequency. The electric signals may be converted into computer readouts, for example, for grading acoustic emission signal being emitted. This invention relates particularly to improvements in such an arrangement wherein a waveguide is utilized for applications where the temperature levels or other conditions involved in the solid object of interest being measured require that the sensor itself and those handling the sensor be spaced from the surface of the object of interest.

That is, the phenomonon of acoustic emission, to which the present invention relates, is concerned with the detection of elastic waves that are emitted from a source within an object and become manifest at positions remote from the source. Such waves are developed, for example, in the cracking of a pressure vessel shell either internally, or on the surface when it is failing or deteriorating. Many times, such pressure vessels operate at extreme high or low temperature levels, and it is necessary to provide a spacing between the sensor and the object in order to protect the sensor from the extreme temperature levels. Other times, the object being examined may be operating at high voltage levels, for example, necessitating that the operator of acoustic emission equipment be spaced from such sources.

Thus, the invention is directed to waveguides which may be used to transmit acoustic signals from the object of interest over a spacing to the sensor, and it is an object of this invention to provide a stable electrical insulation for the operator in high voltage applications, and stable acoustic emission transmission at extreme high or low (i.e. cryogenic) temperature levels, while at the same time not subjecting such applications to dispersive signal propagation and acoustic signal loss. The waveguide serves to transmit signals from the surface of the object of interest to the sensor, and maintain the sensor in a spaced relationship and protected against any undesirable circumstances which may affect the user or the sensor.

In the past, acoustic emission waveguides have been comprised of metal rods, or glass or glass composites for insulation purposes. These have not proved entirely satisfactory because they result in high signal loss from dispersion of the signal in the waveguide, size limitation of the cross section, intrinsic acoustic damping in the prior art material, and acoustic impedance mismatch among the waveguide materials, sensors and structures being tested. Such problems may result in a total signal loss of 10 to 20 dB for a common waveguide of one foot.

With this invention, by contrast, a waveguide is provided which is solid and elongated and provides the desirable electrical and/or temperature spacing necessary from the object of interest to the sensor element while reducing signal loss to around 1 dB for each foot of waveguide. The waveguide is comprised of a member selected from the group consisting of aluminum oxide (alumina) and beryllium oxide. Preferably, aluminum oxide is used because it is substantially less costly. Moreover, aluminum oxide is not electrically and thermally conductive as is beryllium, and its acoustic impedance is in better conformity with that of sensors and routine structures being tested.

This invention will now be described in more detail and other objects and advantages thereof will become apparent from the following description, the accompanying drawings, and the appended claims.

DETAILED DESCRIPTION OF THE INVENTION

Figure 1:
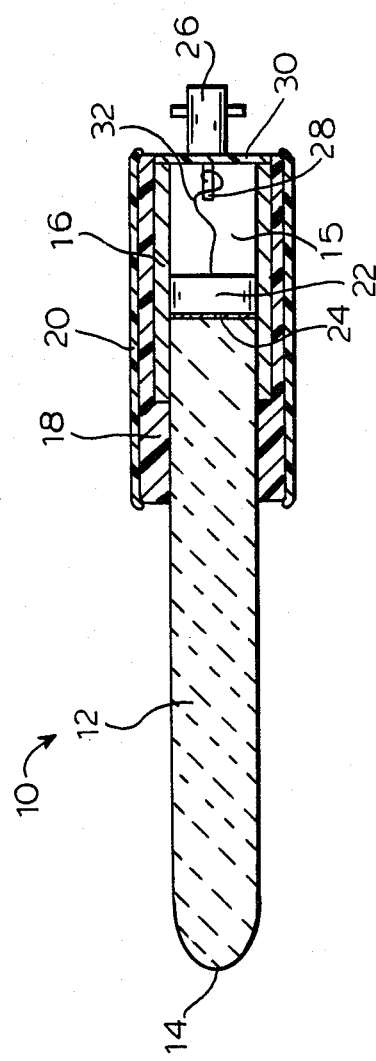
FIG. 1 is a longitudinal sectional view of a waveguide mounted in a hand-held device, and illustrating one form of the invention.

Referring to the drawings in which like reference characters refer to like parts throughout the several views thereof, in FIG. 1 reference numeral 10 designates generally a waveguide illustrating the invention in the form of a hand-held arrangement wherein the waveguide 12 is terminated in a metal case 16 which incorporates therein the sensor 22. Waveguide 12 is comprised of alumina and may have a shaped or formed tip 14 for pinpointing the spot on the surface of a vessel being monitored, for example. Alternatively, the tip may be flat. The sensor element 22 is a piezoelectric crystal.

Material suitable for use as piezoelectric elements include ceramic polycrystalline materials which are polarizable, as well as natural piezoelectric crystals. Such ceramic materials include barium titanate, lead-zironate, lead metaniobate, bismuth titanate, and mixtures thereof with each other or with other suitable materials. Natural crystals for use in the invention include quartz and lithium niobate, etc. Preferably, the crystal utilized in accordance with this invention is lead-zirconate-titanate.

The crystal may be in several shapes, including a plate-like form, a bar form or a truncated cone, for example. Preferably, the crystal is a generally plate form, cylindrical in shape with a diameter of substantially about 0.50 inches, and a thickness of substantially about 0.25 inches.

A conductive epoxy material 24 is coated on the surface of sensor 22 facing the end of alumina waveguide 12. Surrounding the metal casing 16 and a portion of the waveguide 12 is an acoustic isolator material 18 which may be in the form of a synthetic resin form such as polyurethane. The acoustic isolator serves to form a portion of the grip for the hand-held waveguide illustrated in FIG. 1.

Surrounding the foam material 18 is the grip surface 20, which may be comprised of a synthetic resin material, such as polyvinyl chloride web. Extending from the rear plate 30 of the hand-held waveguide structure 10 is the connector 26. Extending internally from plate 30 and connected to connector 26 is a pin 28 to which is connected the lead 32 extending between pin 28 and sensor 22. Material 24 is the ground return in such circuitry.

Figure 2:
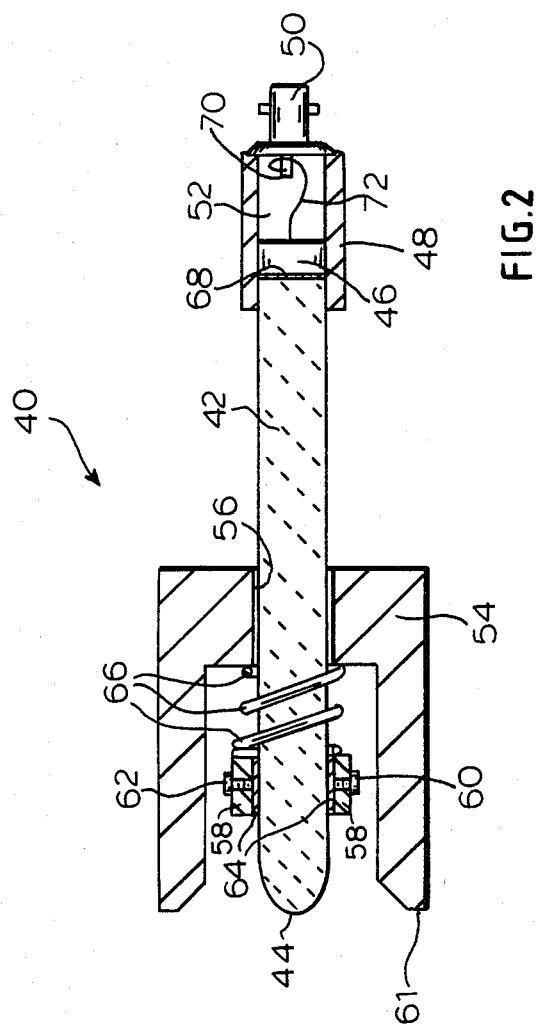
FIG. 2 is a longitudinal sectional view of another embodiment of waveguide illustrating the invention in which the waveguide is mounted in a fixed installation arrangement for mounting on the surface of an object to be examined.

Referring now to FIG. 2, a fixed installation form of waveguide sensor illustrating the invention is shown, generally at 40, having a longitudinal alumina waveguide 42 extending therethrough. The waveguide installation 40 includes a hold down fixture 54 cup shaped but generally U-shaped in section, as shown in FIG. 2 and having a bore 56 for movably mounting the waveguide 42. In this form of the invention, waveguide 42, again may have a shaped tip 44. It will be understood, that it is within the purview of this invention to have a flat end or a pointed tip to waveguide 42, rather than a shaped tip. Mounted on and surrounding a portion of waveguide 42 is a leaf spring 64. Leaf spring 64 is semi-circular in form surrounding a portion of the circumference of the waveguide 42. In this connection, it should be understood that while the illustrated embodiments of waveguides shown in FIGS. 1 and 2 are round, the elongated waveguides may be square or rectangular etc. in cross section.

Leaf spring 64 is held in place surrounding waveguide 42 by a bracket 58 and opposed adjustable screws 60, 62 as shown. The importance of this mounting is to adjust screws 60, 62 so that the leaf spring 64 grips waveguide 42 without any undue pressure being exerted on the surface of waveguide 42. Extending between bracket 58 and fixture 54 is a helical spring 66 which surrounds waveguide 42.

Thus, when the end surface 61 of the fixture 54 is placed against an object of interest, spring 66 will urge the forward engaging point 44 of the waveguide 42 against the surface of interest. In this connection, the mounting fixture 54 may be magnetic, particularly if the object of interest is comprised of a ferrous metal as is the case in many applications of acoustic emission. It will be appreciated that other forms of adherance to the surface of the object being monitored may include, for example, adhesives for holding the hold-down fixture against the surface of the object.

Positioned at the end of waveguide 42 opposite the tip 44, is sensor 46, in the same manner as in the embodiment shown in FIG. 1. Coated on the surface of sensor 46 is a conductive epoxy material. In this connection, the conductive epoxy material 68, is similar to material 24 shown in FIG. 1. Both coatings serve as the ground return in the circuitry extending between the respective connectors such as 50 shown in FIG. 2. The embodiment shown in FIG. 2 includes a connecting pin 70 with a lead 72 extending from sensor 46 to pin 70, in a manner similar to the arrangement shown in FIG. 1. This arrangement also includes a metal casing 48 for containing sensor 46 and the connection between sensor 46 and the end of waveguide 42.

FIGS. 3-6 inclusive illustrate readings from a specific example utilizing the alumina waveguide of the invention as opposed to an arrangement in which there is no waveguide to indicate the very little dispersion of longitudinal waves utilizing the waveguide of the invention versus no waveguides and wherein a transmitter and a receiver transducer arrangement was utilized. In this comparative arrangement, a Dunegan/Endevco S140-type piezeoelectric crystal sensor element (Endevco Corporation, San Juan Capistrano, Calif.) was used, with that crystal being 0.5 inches in diameter. An aluminum oxide rod of a diameter of 0.500 inches was utilized. The waveguide was 28 inches long and was found to provide very little dispersion of longitudinal waves as discussed above. Each signal was clearly identifiable even after seven reflections. The attenuation between the use of a waveguide application of the non-use thereof is observed to be about 1 dB per foot. The waveguide/sensor pair was calibrated on a spark impulse calibration system and the results obtained are shown in the FIGS. 3-6.

Figure 3:
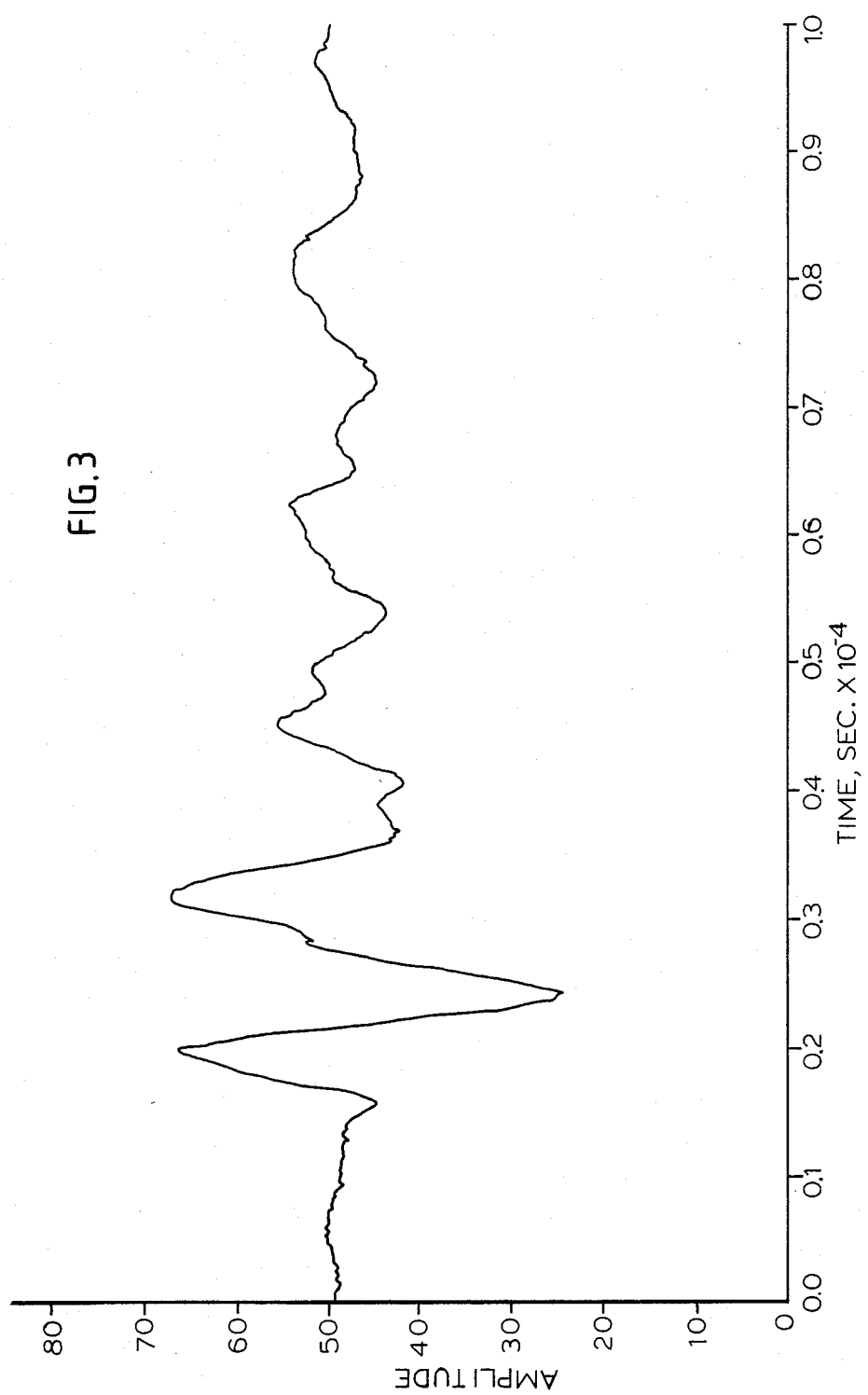
FIG. 3 is a response waveform from a sensor mounted directly on a calibration block and excited by a spark impulse source.
Figure 4:
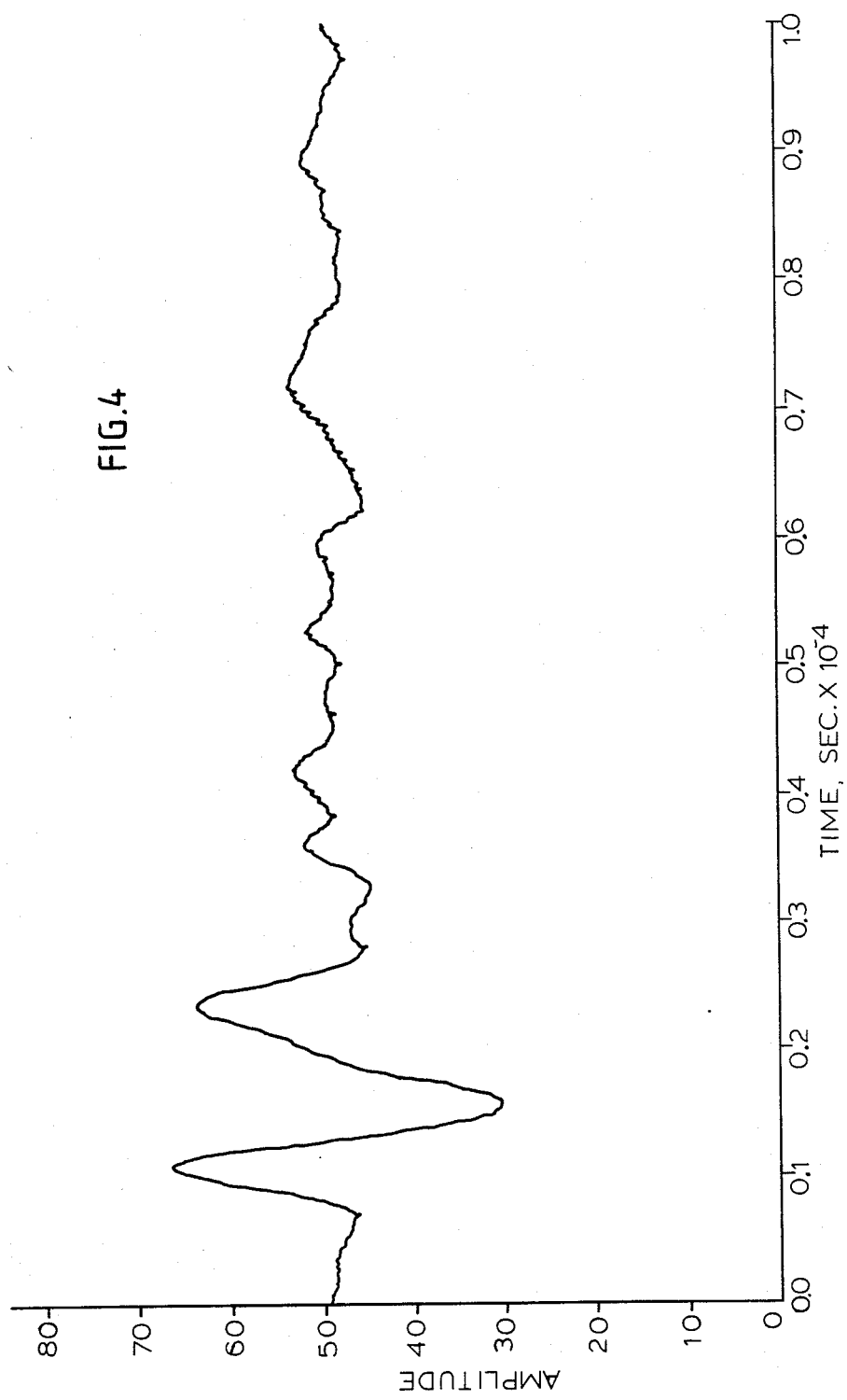
FIG. 4 is a response waveform similar to that of FIG. 3 but with the sensor mounted on a 28 inch alumina waveguide coupled to the calibration block and excited by the spark.
Figure 5:
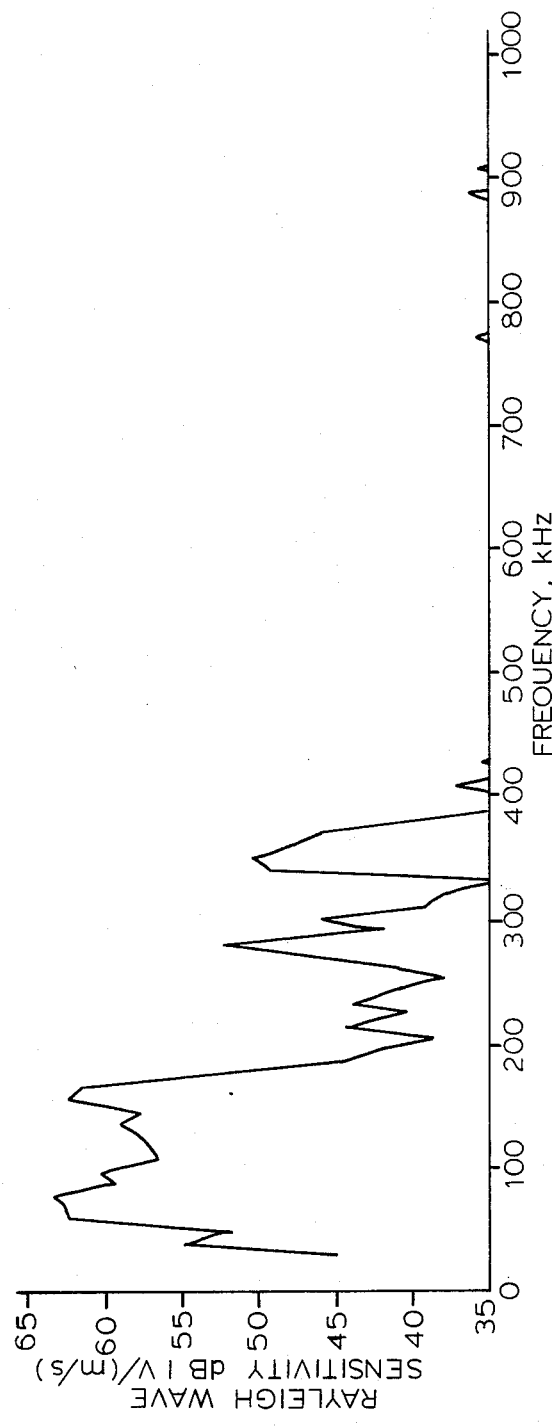
FIGS. 5 and 6 show the corresponding frequency spectrums for the waveforms shown in FIGS. 3 and 4.
Figure 6:
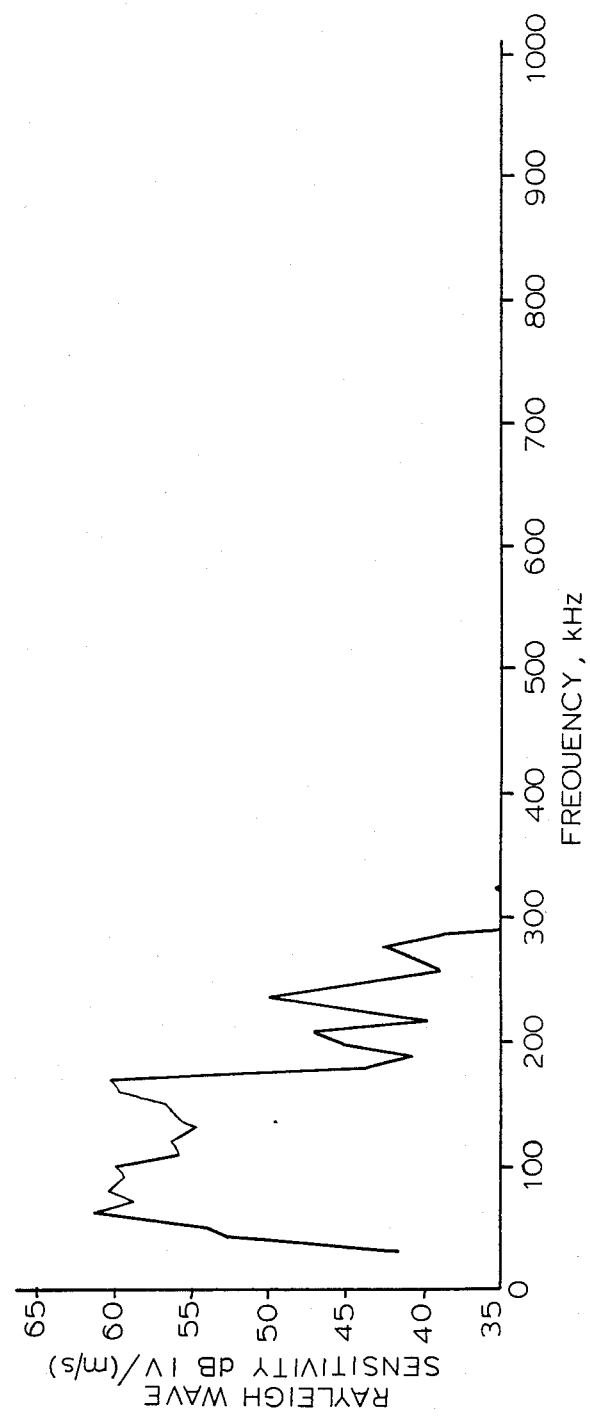

FIGS. 3 and 4 show the waveform of the sensor and the waveguide-sensor, respectively. FIGS. 5 and 6 show the corresponding frequency spectrums. From the above we can see that the wave forms are quite similar and so are the spectrums. However, on the spectrum plots there is an attenuation of about 3 dB for the waveguide. This compares favorably with a routine loss of about 20 dB for a conventional waveguide.

Thus, there is provided, in accordance with this invention, a waveguide which allows for mounting a sensor safely away from a hostile environment, so that a sensor of limited environmental capability can be used if it is otherwise desirable. Moreover, the waveguide of the invention provides access to an otherwise inaccessible test location wherein limited space for the mounting of a regular sensor is involved. If for example a high voltage transformer is the object of interest to be measured for acoustic emission, the waveguide of the invention avoids human contact with such a dangerous test part. Moreover, the invention maximizes a signal-to-noise ratio in some difficult environments as an engineering compromise, where unwanted signals from outside noise is unavoidable.

In selecting the dimensions for a specific waveguide application, as discussed above, lower frequencies allow larger diameter waveguides and vice versa. For example, if one is only interested in an acoustic emission signal below 100 kHz, a waveguide with a diameter of 1.500 inches may be used. Conversely, the same relation yields a waveguide diameter of only 0.150 inches if one wants to go to 1 MHz. From a practical standpoint, a waveguide will be selected to have a cross sectional dimension either in diameter or side-by-side as large or slightly larger than the piezoelectric crystal to be utilized in order to realize maximum sensitivity. A waveguide with a diameter much larger than the crystal can only be justified for other reasons.

With respect to the length of the waveguide, theoretically, it can be as long as one desires. However, the wave propagation loss is about 1 dB per foot, as discussed above. Obviously, the longer the waveguide the greater the total loss. In practice, a waveguide will be utilized which is as short as necessary for a specific application as will be understood by practitioners-in-the-art. Obviously, with a less total wave propagation loss, a short waveguide is generally much easier to handle and simpler to mount on the surface. For waveguides designed for heat insulation, the waveguide may be only a few inches longer than the thickness of the insulation. That is, a sensor installed six inches above the heat insulation will probably stay cool enough for most measurement purposes. For a high voltage transformer acoustic emission test, for example, a length of 1.5 feet up to 3 feet in length may be in order, to insure operator safety, as will be understood.

While the apparatus herein disclosed forms a preferred embodiment of this invention, this invention is not limited to that specific apparatus and changes can be made therein without departing from the scope of the invention which is defined in the appended claims. For example, the hand-held device may include a pistol-type handle or similar such arrangement for easy manipulation of the device.

What is claimed is:

1. Waveguide apparatus for examining acoustic emission signals from objects of interest, comprising:
   (a) an elongated solid waveguide body having first and second ends;
   (b) a piezoelectric sensor mounted on said first end of said body;
   (c) electrical connection means connected to said sensor for containing said apparatus to acoustic emission signal response mechanisms;
   (d) a cup-shaped magnetic hold-down fixture connected to said body for holding said second end of said body against an object to be examined said hold-down fixture being connected one the end of said body opposite said sensor with said body being mounted for relative longitudinal movement in said hold-down fixture;
   (e) said body being made of a material selected from the group consisting of aluminum oxide and beryllium oxide;
   (f) resilient means mounted between said hold-down fixture and said body for urging one end of said body against in object of interest.

2. The apparatus of claim 1, wherein:
   (a) said body is aluminum oxide.

3. Waveguide apparatus for examining acoustic emission signals from objects of interest comprising:
   (a) an elongated solid waveguide body having first and second ends;
   (b) a piezoelectric sensor mounted on said first end of said body;
   (c) electrical connection means connected to said sensor for connecting said apparatus to acoustic emission signal response mechanisms;
   (d) a hand-grip connected to said body adjacent said sensor on said body for holding said second end of said body against an object to be examined, said hand-grip comprising
      (1) a metallic body around said sensor, the adjacent end of said body, and said electrical connection means; and
      (2) a foamed insulation layer around said metallic body; and
      (3) a synthetic resin layer around said foamed insulation layer
   (e) said body being made of a material selected from the group consisting of aluminum oxide and beryllium oxide.

4. The apparatus of claim 1, wherein:
   (a) said sensor is cylindrical in shape; and
   (b) said elongated body is cylindrical in shape.

5. The apparatus of claim 1, wherein:
   (a) the cross-sectional dimensions of said sensor and body are substantially the same.

* * * * *

UNITED STATES PATENT AND TRADEMARK OFFICE
CERTIFICATE OF CORRECTION

PATENT NO. : 4,510,812
DATED : April 16, 1985
INVENTOR(S) : Feng

It is certified that error appears in the above-identified patent and that said Letters Patent are hereby corrected as shown below:

Column 1, line 40, please correct "Thus, the invention" to --Thus, this invention-- .

Column 2, line 67, please correct "resin form" to --resin foam-- .

Column 4, line 17, please correct "the waveform of" to --the waveforms of-- .

Column 4, line 49, please correct "or side-by-side" to --side-to-side-- .

Column 5, line 22, please correct "for containing" to --for connecting-- .

Column 5, line 28, please correct "one the end" to --on the end-- .

Signed and Sealed this

Fifteenth Day of October 1985

[SEAL]

Attest:

Attesting Officer

DONALD J. QUIGG

Commissioner of Patents and Trademarks—Designate